United States Patent [19]

Rattner et al.

[11] Patent Number: 4,947,830

[45] Date of Patent: Aug. 14, 1990

[54] SHOCK WAVE GENERATOR FOR EXTRACORPOREAL LITHOTRIPSY

[75] Inventors: Manfred Rattner, Grossenseebach; Benedikt Hartinger, Nuremberg, both of Fed. Rep. of Germany

[73] Assignee: Siemens Aktiengesellschaft, Berlin and Munich, Fed. Rep. of Germany

[21] Appl. No.: 298,755

[22] Filed: Jan. 19, 1989

[30] Foreign Application Priority Data

Feb. 16, 1988 [DE] Fed. Rep. of Germany ... 8801989[U]

[51] Int. Cl.[5] .......................... A61B 8/00; A61B 17/22

[52] U.S. Cl. ............................... 128/24 A; 128/660.03

[58] Field of Search ................ 128/328, 24 A, 660.03; 367/150, 155, 157; 606/127, 128

[56] References Cited

U.S. PATENT DOCUMENTS

| | | | |
|---|---|---|---|
| 2,559,227 | 7/1951 | Rieber | 128/24 A |
| 3,039,078 | 6/1962 | Wilcoxon et al. | |
| 4,674,505 | 6/1987 | Pauli et al. | |
| 4,834,106 | 5/1989 | Hassler et al. | 128/660.03 |
| 4,836,191 | 6/1989 | Noske et al. | 128/24 A |

FOREIGN PATENT DOCUMENTS

| | | | |
|---|---|---|---|
| 0131653 | 1/1985 | European Pat. Off. | 128/328 |
| 0286170 | 10/1988 | European Pat. Off. | 128/328 |
| 2902331 | 7/1980 | Fed. Rep. of Germany | 128/24 A |
| 3328068 | 2/1985 | Fed. Rep. of Germany | 128/328 |
| 3532678 | 3/1987 | Fed. Rep. of Germany | 128/24 A |
| 8703797 | 7/1987 | PCT Int'l Appl. | 128/328 |

*Primary Examiner*—Lee S. Cohen

*Assistant Examiner*—Krista M. Pfaffle

*Attorney, Agent, or Firm*—Hill, Van Santen, Steadman & Simpson

[57] ABSTRACT

A shock wave generator of the type suitable for use in an extracorporeal lithotripsy treatment of calculi in a patient permits the shock wave generator to be applied to the body surface of the patient, while still permitting adjustment, i.e., displacement, of the focus without removing the shockwave generator from the body surface. For this purpose, the shock wave source is adjustable relative to the housing of the shock wave generator. When the housing, together with the flexible sack which terminates the housing, is acoustically applied to the body surface of the patient, the shock wave source can still be moved within the housing without changing the application to the patient. Additionally, an ultrasound locating system can be arranged in the shock wave source, which can be adjustable in combination with the shock wave source for precisely, locating, or relocating, the calculus to be disintegrated.

8 Claims, 2 Drawing Sheets

SHOCK WAVE GENERATOR FOR EXTRACORPOREAL LITHOTRIPSY

BACKGROUND OF THE INVENTION

1. Field of the Invention

The present invention is directed to a shock wave generator of the type used in extracorporeal lithotripsy treatment of a patient, and in particular to such a shock wave source having a housing terminating in a flexible sack which covers the exit opening for the shock waves, the sack limiting a coupling volume filled with a coupling fluid.

2. Description of the Prior Art

A shock wave generator in the form of a shock wave tube having an exit opening for the shock waves which is covered by a flexible sack, which is disposed against the body surface of a patient to be treated, is disclosed in German AS No. 33 28 051, corresponding to U.S. Pat. No. 4,674,505. The flexible sack limits a volume which is filled with a coupling fluid to assist coupling of the shock waves to the body of the patient. In this known shock wave generator, the shock wave source is mounted stationary with respect to the housing. The entire shock wave generator must therefore be displaced to set, or reset, the focus. If, for example, the shock wave generator is acoustically applied to the surface of the patient via the flexible sack and a gel disc, and if a displacement of the focus is thereafter required, a decoupling of the shock wave generator and a repeated acoustic application must be undertaken. The examining personnel are burdened as a result, and the treatment is prolonged.

SUMMARY OF THE INVENTION

It is an object of the present invention to provide a shock wave generator having a shock wave source with a housing terminated by a flexible sack which does not require displacement of the entire shock wave generator from an initially set position if the focus of the shock wave generator requires displacement, within predetermined limits.

The above object is achieved in accordance with the principals of the present invention in a shock wave generator wherein the shock wave source is mounted adjustably relative to the housing. In the shock wave generator disclosed herein, it is possible to undertake a displacement of the focus, and thus achieve an optimum focus setting, by adjusting the shock wave source within its housing, while maintaining the housing stationary, i.e., at its acoustically applied position, relative to the patient.

Moreover, application of the shock wave generator to the patient, given a stationary focus, can be undertaken by adjusting the housing, including the sack, relative to the shock wave source. The position of the focus does not change if this type of adjustment is undertaken.

In one embodiment of the invention, the shock wave source is connected to a centrally disposed locating system, and is mounted adjustably in combination therewith. A precise locating, or relocating, is thus possible by adjusting the locating system while the shock wave generator remains in its acoustically applied position. If, as a result of the locating, it is determined that the focus does not have the desired position relative to the calculus to be disintegrated, an automatic follow-up of the focus, by adjusting the shock wave source, can be undertaken using output signals from the locating system.

DESCRIPTION OF THE PREFERRED EMBODIMENTS

Figure 1:
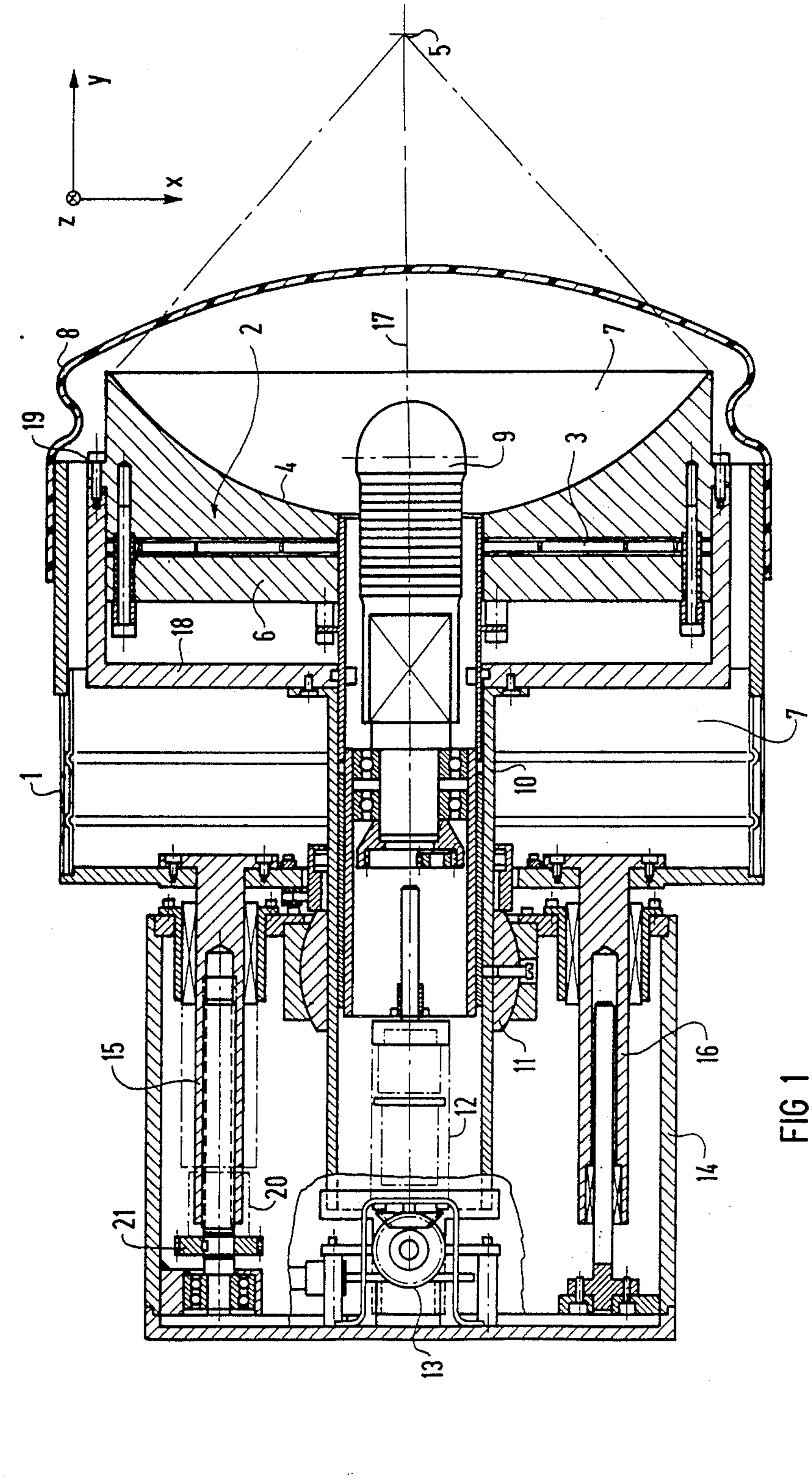
FIG. 1 is a longitudinal sectional view of a shock wave generator constructed in accordance with the principles of the present invention.

As shown in the drawing, a shock wave generator constructed in accordance with the principals of the present invention includes a housing 1 in which a shock wave source 2 in a holder 18 is disposed. The shock wave source 2 includes a piezoelectric crystal 3, which directs shock waves onto a focus 5 via an acoustic lens 4. An acoustic load or absorber 6, which absorbs the shock waves emitted at the rear of the crystal 3, is mounted behind the crystal 3.

The coupling volume 7 in the housing 1 is filled with a coupling liquid, for example water. The end of the housing 1 from which the shock waves are emitted is closed by a flexible sack 8, which permits the shock wave generator to be acoustically applied to the body surface of a patient to be treated.

The shock wave generator also includes an ultrasound locating system 9, disposed centrally within the shock wave source 2. The ultrasound locating system 9 is rotatably seated for locating the calculus to be disintegrated. Together with the shock wave source 2, it is connected to a tube 10 which is seated by means of a ball and socket joint 11 so as to be pivotable around two perpendicularly intersecting axes, so that the tube 10 is movable in two planes. The two planes are the x-y and y-z planes, with reference to the Cartesian coordinate axes shown in the drawing. Adjustment of the tube 10 in each of these planes is undertaken with a gearing 13 operated by an electric motor 12.

The housing 1 is connected to a holder 14 by guides 15 and 16. The guide 15 may be in the form of a threaded spindle which, when rotated by a motor 20 engaging a gear 21, permits the housing 1, together with the shock wave source 2, to be adjusted relative to the holder 14 in a direction perpendicular to the aforementioned two perpendicularly intersecting axes, which is the direction of the longitudinal axis 17 (i.e., in the y direction).

Figure 2:
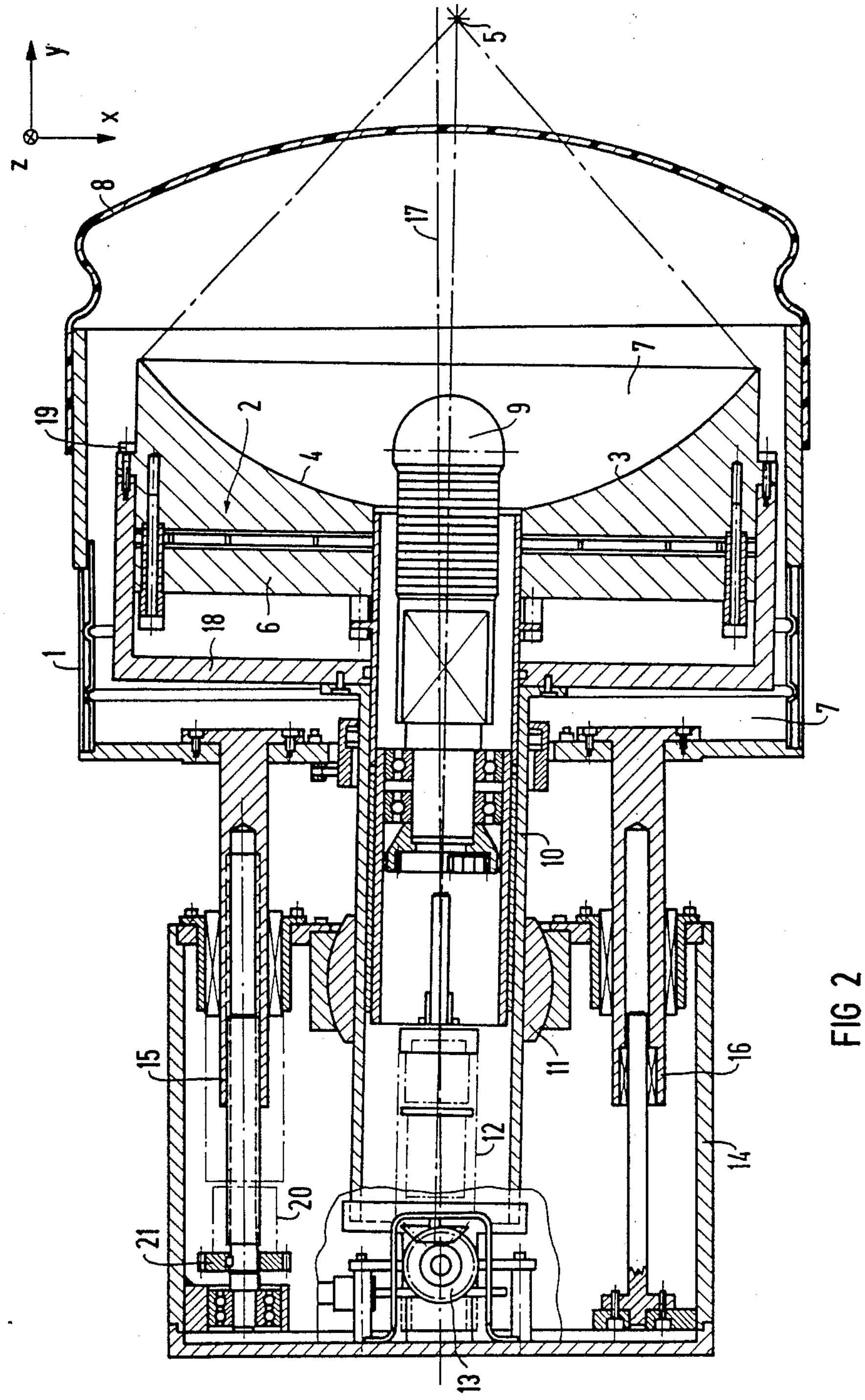
FIG. 2 is a longitudinal sectional view of a shock wave generator constructed in accordance with the principles of the present invention showing the housing displaced relative to the shock wave source and the holder, and with the shock wave source canted.

For shock wave treatment, the housing 1 is brought to the body surface of a patient using the guides 15 and 16 to an extent such that the sack 8 is in contact with the body surface. A reflection-free sound transition is achieved by the known procedure of inserting a gel disc between the sack 8 and the body surface. Adjustment of the shock wave source 2 together with the ultrasound locating system 9 is then undertaken independently of the positioning of the housing 1, by pivoting the tube 10 in one or both of the x-y and y-z planes, as shown in FIG. 2.

When the shock wave generator is applied to the patient, it is possible as described above to displace the focus 5 within predetermined limits, i.e., to bring it into coincidence with the calculus to be disintegrated. The position of the calculus can be located using the ultrasound locating system 9, and the focus can then be correspondingly set. Such focus adjustment can be undertaken automatically using the motors, such as the motor 12, and the gearing 13, which drive the tube 10.

During treatment, a suitable pivoting of the tube 10, including the shock wave source 2, enables positioning of the focus 5 on a predetermined path. The motors, such as the motor 12, are correspondingly driven for this purpose. A range of focus having a predetermined extent can thus be scanned, and an artificial enlargement of the focus can be achieved in this manner.

The relative of adjustability of the housing 1 and the shock wave source 2, together with the ultrasound locating system 9, in the direction of the axis 17 offers the following possibilities. When the shock wave generator is applied to the patient, an adjustment of the focus is possible by adjusting shock waves source 2 in the housing 1. The housing 1 and the sack 8 do not change position relative to the patient Given an isocentric operating mode, i.e., given a spatially rigidly prescribed position of the focus, the housing 1 and the sack 8 are displaceable for the best application to the body surface of the patient.

The shock wave source 2 in the illustrated exemplary embodiment is shown as a piezoelectric shock wave source. Instead of such a piezoelectric shock wave source, a different type of shock wave source, such as an electrodynamic shock wave source, may be used, wherein the shock waves are generated by a membrane operating in combination with a flat coil, to which high voltage pulses are supplied. The shock wave source 2 is interchangeably arranged in a mount 18 using a screw-type connection 19, so that the desired shock wave source may be used.

Although changes and modifications may be suggested by those skilled in the art, it is the intention of the inventors to embody within the patent warranted hereon all changes and modifications as reasonably and properly come within the scope of their contribution to the art.

We claim as our Invention:

1. A shock wave generator for extracorporeal lithotripsy comprising:
- a housing;
- a shock wave source in said housing, said shock wave source having a central longitudinal axis and including means for focusing shock waves to a focus disposed on said longitudinal axis;
- a flexible sack covering an end of said housing adapted for contact with the body of a patient, and defining a coupling volume on combination with said housing and said shock wave source;
- an acoustic coupling fluid filling said coupling volume; and
- means for adjustably mounting said shock wave source relative to said housing for permitting pivoting of said longitudinal axis independently of the position said housing and said sack thereby to adjust the location of said focus relative to said housing and said sack while maintaining said sack in contact with said patient.

2. A shock wave generator as claimed in claim 1 wherein said means for adjustably mounting said shock wave source relative to said housing is a means for adjustably mounting said shock wave source in said housing.

3. A shock wave generator as claimed in claim 1 wherein said shock wave generator further comprises a holder for said housing, and means for mounting said housing to said holder, and wherein said means for adjustably mounting said shock wave source is further defined as means in said holder for permitting pivoting of said longitudinal axis around two perpendicularly intersecting axes, independently of the position of said housing and said sack thereby to adjust the location of said focus relative to said housing and said sack.

4. A shock wave generator as claimed in claim 3 wherein said means for mounting said housing to said holder is further defined as means in said holder and attached to said housing for displacing said housing and said shock wave source together relative to said holder in a direction defined by the intersection of said two planes.

5. A shock wave generator as claimed in claim 1 further comprising:
- means for locating in said patient, a calculus to be disintegrated mounted in said shock wave source, and being comovable with said shock wave source by said means for adjustably mounting said shock wave source.

6. A shock wave generator as claimed in claim 1 further comprising motor means for driving said means for adjustably mounting said shock wave source for moving said focus within a predetermined region.

7. A shock wave generator as claimed in claim 1 wherein said means for adjustably mounting said shock wave source relative to said housing includes means for removably attaching said shock wave source to said means for adjustably mounting, to permit removal and replacement of a shock wave source.

8. A shock wave generator for extracorporeal lithotripsy comprising:
- a housing;
- a shock wave source in said housing, said shock wave source having a central longitudinal axis and including means for focusing shock waves to a focus disposed on said longitudinal axis;
- a flexible sack covering an end of said housing for application to the body of a patient, and defining a coupling volume in combination with said housing and said shock wave source;
- an acoustic coupling fluid filling said coupling volume;
- a holder for said housing;
- means disposed in said holder and extending from said holder through an opening in said housing into an interior of said housing for adjustably mounting said shock wave source relative to said housing for permitting pivoting of said longitudinal axis around two perpendicularly intersecting axes independently of the position of said housing and said sack, thereby to adjust the location of said focus relative to said housing and said sack while maintaining said sack in contact with said patient; and
- means disposed in said holder and attached to said housing for displacing said housing relative to said shock wave source and said holder along a direction perpendicular to both of said two perpendicularly intersecting axes.

* * * * *